United States Patent [19] [11] 4,034,010
Hamano et al. [45] July 5, 1977

[54] BIS-(META-AMIDINOPHENOXY)-COMPOUNDS AND PHARMACOLOGICALLY ACCEPTABLE ACID ADDITION SALTS THEREOF

[75] Inventors: Sachiyuki Hamano, Tokyo; Tamotsu Kanazawa, Tokorozawa; Shin-ichi Kitamura, Tokyo, all of Japan

[73] Assignee: Eisai Co., Ltd., Tokyo, Japan

[22] Filed: Sept. 22, 1976

[21] Appl. No.: 725,673

[30] Foreign Application Priority Data
Jan. 13, 1976  Japan ................. 51-2458

[52] U.S. Cl. ............. 260/564 R; 260/456 A; 260/501.14; 424/303; 424/316; 424/326
[51] Int. Cl.² ................. C07C 123/00

[58] Field of Search ....... 260/564 R, 501.14, 456 A

[56] References Cited
UNITED STATES PATENTS

| | | | |
|---|---|---|---|
| 2,277,862 | 3/1942 | Ewins et al. | 260/564 R |
| 2,449,724 | 9/1948 | Short et al. | 260/564 R |
| 3,105,853 | 10/1963 | McKay et al. | 260/564 R |

*Primary Examiner*—Gerald A. Schwartz
*Attorney, Agent, or Firm*—Wenderoth, Lind & Ponack

[57] ABSTRACT

Bis-(meta-amidinophenoxy)-compounds and pharmacologically acceptable acid addition salts thereof, having excellent antifungal, antibacterial and anti-trichomonal activities.

2 Claims, No Drawings

BIS-(META-AMIDINOPHENOXY)-COMPOUNDS AND PHARMACOLOGICALLY ACCEPTABLE ACID ADDITION SALTS THEREOF

This invention relates to a novel bis-(meta-amidinophenoxy)-compound and a pharmacologically acceptable acid addition salt thereof which is represented by the general formula:

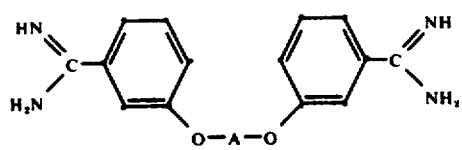
(I)

wherein A represents a chain residue selected from the group consisting of

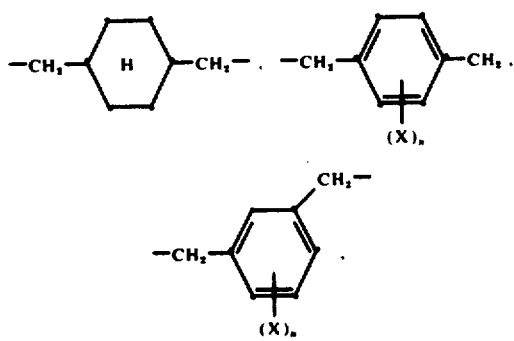

$-CH_2-CH=CH-CH_2-$, $-(CH_2)_2S(CH_2)_2-$, and $-(CH_2)_m-$, in which X represents chlorine atom, n is an integer of 0 to 4, and m is an integer of 4 to 6. As the pharmacologically acceptable acid addition salt, there may be mentioned for example, inorganic acid addition salts such as hydrochloride, hydrobromide, sulfate, bisulfite and the like; and, for example, organic acid addition salts such as acetate, maleate, fumalate, citrate, succinate, lactate, tartarate, oxalate, methane sulfonate and the like.

The compound (I) according to this invention has an excellent antifungal, antibacterial and anti-trichomonal activities, whereby it is effective for the treatment of the infection of fungi such as Candida, Cryptococcus, and the like; infection of various bacteria; and Trichomonas.

The compound (I) according to this invention can be prepared by applying the so called "Pinner amidine synthesis" [J. Am. Chem. Soc. 77, 2341 (1955)], in accordance with the following reaction sequence:

Step 1:

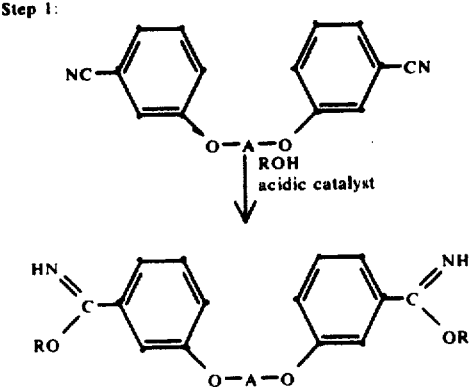

Step 2:

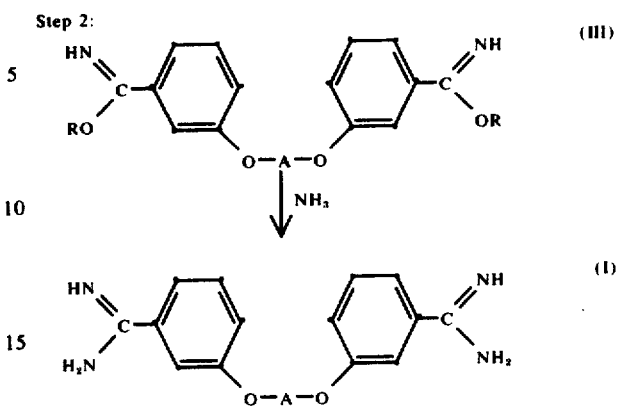

wherein A has the same meanings as defined above, and R represents a lower alkyl group.

More particularly, the compound (I) is prepared by the step 1 in which bis-(meta-cyanophenoxy)-compound (II) is reacted with a lower alcohol such as methanol, ethanol, propanol, isopropanol, butanol and the like in the presence of an acidic catalyst to yield the corresponding bis-(meta-lower alkoxycarboimidophenoxy)-compound (III); and followed by the step 2 in which said intermediate compound (III) is treated with an ammonium compound to yield the bis-(meta-amidinophenoxy)-compound (I) of this invention.

In the step 1, the reaction is effected by dissolving the compound (II) in a solvent, adding a calculated amount of the lower alcohol to said solution, and further adding the acidic catalyst, followed by allowing to stand the solution at a room temperature.

As the solvent used in the step 1, there may be exemplified an organic solvent including a halogenated hydrocarbon solvent such as chloroform, carbon tetrachloride, dichloromethane, dichloroethane, trichloroethylene and the like; an aromatic hydrocarbon solvent such as benzene, nitrobenzene, toluene, xylene and the like; an ether solvent such as diethyl ether, diisopropyl ether, tetrahydrofuran, dioxane, diglyme and the like. The solvents may be used, by properly selecting from such solvents, in a form of a sole solvent or a mixed solvent. Alternatively, an excess of the lower alcohol may be used in place of a solvent. The acidic catalysts used in this step include dry hydrochloric acid, boron trifluoride, sulfonic acid and the like. The product of this step is obtained in a form of the acid addition salt form of the compound (III). The compound (III) can be provided as the source material for the step 2, in a form of the acid addition salt per se, or in a freed form. Usually, the compound (III) is used for the step 2 as it is, without isolation and purification.

The step 2 is effected by dissolving the compound (III) in the same solvent as that of the step 1, and subjecting to the reaction with an ammonium compound. The ammonium compound used may be ammonia per se or an ammonium salt such as ammonium chloride, ammonium sulfate, ammonium carbonate and the like. The product of the step 2 is the desired final compound (I) of this invention.

The compound (II), the starting material for the preparation of the compound (I) according to this invention is also a novel compound, which is synthesized according to the following reaction sequence:

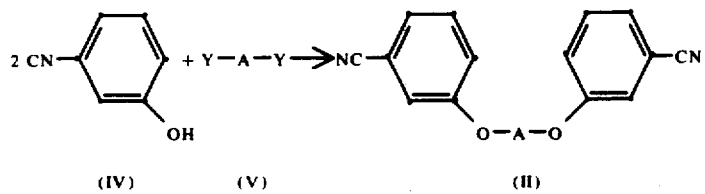

(IV)   (V)   (II)

wherein A has the same meanings as defined above, Y represents a halogen atom, methanesulfonyloxy group or tosyloxy group.

Bis-(meta-cyanophenoxy)-compound (II) is produced by reacting meta-cyanophenol (IV) with the compound (V) in the presence of an alkali.

As the solvent, there may be used an organic solvent including an alcoholic solvent such as methanol, ethanol, propanol, isopropanol and the like; and an amidic solvent such as dimethyl acetamide, dimethyl formamide, hexamethyl phosphoramide and the like. The solvent(s) may be selected from such solvents, and may be used in a form of a sole solvent or a mixed solvent.

The compound (I) of this invention has an excellent antifungal, antibacterial and anti-trichomonal activities. These activities are clearly proved by the following results of pharmacological tests.

The compounds under test:
i. The compound for control: Nystatin
ii. The compound according to this invention:
1,4-Bis-(m,m'-amidinophenoxymethyl)-cyclohexane-dihydrochloride (hereinafter refer to compound A of this invention)

PHARMACOLOGICAL TEST 1

Antifungal Test

Procedure of the test:

Repective agar plates were prepared by dissolving compounds under test in aseptic water to make a two fold dilution series, taking each one milliliter of said diluted solutions and 9 ml of Sabouraud medium into a petri dish, and sufficiently admixing the same.

On the other hand, an inoculum was prepared by cultivating an examined fungus (microorganism) on the Sabouraud slant medium and suspending two loopful of the incubated fungus in 10 ml of sterilized physiological saline water.

One loopful of the inoculum was streaked on the abovementioned agar plate. After the agar plate was incubated at a defined temperature for a predetermined period of time to determine the minimal inhibitory concentration (M.I.C.).

RESULTS OF THE TEST

1. Antifungal activity
Incubation conditions
Incubation temperature: 27° C.
Incubation time: 3 days (72 hours) and 7 days (168 hours)

Table 1

Minimal inhibitory concentration against various fungi

| Microorganism | M.I.C. (μg/ml) Compound A according to this invention | |
|---|---|---|
| | 3 days incubation | 7 days incubation |
| Candida albicans AHU 3656 | 3.13 | 6.25 |
| Candida albicans NAKAGAWA IFM 4017 | 3.13 | 3.13 |
| Candida albicans Yu-1200 IFM 4020 | < 1.56 | 3.13 |
| Candida albicans IFM 4080 | 3.13 | 6.25 |
| Candida tropicalis AHU 3071 | 3.13 | 3.13 |
| Candida utilis AHU 3053 | 3.13 | 3.13 |
| Candida guilliermondii AHU 3654 | 25 | 25 |
| Cryptococcus neoformans | 3.13 | 3.13 |
| Saccharomyces cerevisiae | < 1.56 | < 1.56 |

(2) Anticandida activity
Incubation conditions
Incubation temperature : 37° C.
Incubation time : 3 days (72 hours)

Table 2

Minimal inhibitory concentration against Candida alibicans

| Microorganism | M.I.C. (μg/ml) | |
|---|---|---|
| | Nystatin | Compound A according to this invention |
| Candida albicans AHU 3656 | 6.25 | 3.13 |
| Candida albicans Yu-1200 IFM 4020 | 6.25 | 0.8 |
| Candida albicans NAKAGAWA IFM 4017 | 6.25 | 1.56 |

(3) Effect of incubation temperature on the antifungal activity
Incubation conditions:
Incubation temperature: 27° C.
Incubation time 3 days (72 hours)
Incubation time 7 days (168 hours)
Incubation temperature: 37° C.
Incubation time 2 days (48 hours)
Incubation time 3 days (72 hours)

Table 3

Minimal inhibitory concentration of Compound A of this invention

| Incubation conditions Microorganism | M.I.C. (μg/ml) | | | |
|---|---|---|---|---|
| | 27° C. | | 37° C. | |
| | 3 days | 7 days | 2 days | 3 days |
| Candida albicans AHU 3656 | 3.13 | 6.25 | 3.13 | 3.13 |
| Candida albicans NAKAGAWA IFM 4017 | 3.13 | 3.13 | 0.8 | 1.56 |
| Candida alibicans Yu-1200 IFM 4020 | 1.56 | 3.13 | 0.8 | 0.8 |
| Candida albicans IFM 4080 | 3.13 | 6.25 | 0.8 | 3.13 |

In viewpoint of the result of the pharmacological test 1, it is apparent that the compound A of this invention has an excellent antifungal activity against the yeast-like fungi such as Candida, Cryptococcus, and the activity is not influenced by the incubation temperature. In addition, it is recognized that the compound A of this invention has a more excellent anti-candida activity than that of the nystatin.

PHARMACOLOGICAL TEST 2

Antifungal test when a serum is added.

Procedure of the test:

Minimal inhibitory concentration (M.I.C.) was determined by preparing the agar plate medium in the same manner of the preceding pharmacological test 1, except for the addition of the horse serum. The concentration of the component in the medium was finally corrected, so that it may amount to the concentration of the component when the horse serum was not added.

RESULTS OF THE TEST

Incubation conditions

Incubation temperature: 27° C

Incubation period: 3 days (72 hours) 7 days (168 hours)

Table 4

Minimal inhibitory concentration of the compound A of this invention when the serum was added ($\mu$g/ml)

| Microorganism | M.I.C. ($\mu$g/ml) of serum added | | | | | |
|---|---|---|---|---|---|---|
| | 0 % | | 10 % | | 30 % | |
| | 3 days | 7 days | 3 days | 7 days | 3 days | 7 days |
| Candida albicans AHU 3656 | 3.13 | 6.25 | 25 | 25 | 25 | 25 |
| Candida albicans NAKAGAWA IFM 4017 | 3.13 | 3.13 | 25 | 25 | 6.25 | 6.25 |
| Candida albicans Yu-1200 IFM 4020 | <1.56 | 3.13 | 6.25 | 6.25 | 25 | 25 |
| Candida albicans IFM 4080 | 3.13 | 6.25 | 12.5 | 12.5 | 12.5 | 12.5 |
| Candida tropicalis AHU 3071 | 3.13 | 3.13 | 6.25 | 6.25 | 12.5 | 12.5 |
| Candida utilis AHU 3053 | 3.13 | 3.13 | 3.13 | 6.25 | <0.8 | <0.8 |
| Candida guillier-mondii AHU 3654 | 25 | 25 | 25 | 25 | 50 | 50 |
| Candida Krusei AHU 3993 | >100 | >100 | 200 | >200 | 100 | 100 |
| Cryptococcus neoformans | 3.13 | 3.13 | 6.25 | 12.5 | 12.5 | 12.5 |

From the results of the pharmacological test 2, it is noted that the antifungal activity of the compound A of this invention, when 10% and 30% by volume of the horse serum was added to the agar plate medium for test, is nearly same as that when the horse serum was not added; or slight difference to the extent of 1 – 2 dilution step(s). It is therefore shown that the antifungal activity of the compound A of this invention is hardly affected by the addition of the horse serum.

PHARMACOLOGICAL TEST 3

Antibacterial test

Procedure of the test:

A compound under test was dissolved in aseptic water to prepare a two fold dilution series. Each one milliliter of the solution was taken in a petri dish. Nine ml of infusion agar medium (Difco) was added to the solution, thereby preparing the agar plate for test. A pre-culture of each test strain in Tripticase soy broth medium (BBL) at 37° C. for 18 hours was streaked on the above-mentioned agar plate, and the said agar plate was incubated at 37° C. for 18 hours to determine the minimal inhibitory concentration (M.I.C.).

RESULTS OF THE TEST

Table 5

Minimal inhibitory concentration of the compound A of this invention

| Microorganism | M.I.C. ($\mu$g/ml) |
|---|---|
| Staphylococcus aureus 209-P JO-1 | 3.13 |
| Staphylococcus aureus 13-6 | 6.25 |
| Streptococcus hemolyticus Y-73-5 | 6.25 |
| Escherichia coli NIHJ JC-1 | 100 |
| Escherichia coli E-15 | 200 |
| Salmonella typhimurium 1406 | 200 |
| Klebsiella pneumonial NO-1 | 200 |
| Proteus mirabilis OM-1 | >200 |
| Pseudomonas aeruginosa | >200 |

The compound A of this invention showed a strong antibacterial activity in that minimal inhibitory concentration against Staphylococcus aureus 209-P, Staphylococcus anreus 13-6 and Streptococcus pyogenes amounts to 3.13 – 6.25 $\mu$g/ml. The compound A also showed, though it is rather weak, the antibacterial activity in that minimal inhibitory concentration against gram-negative bacteria such as Escherichia coli NIHJ and Escherichia coli E-15 amounts to 100 – 200 $\mu$g/ml or above 200 $\mu$g/ml.

PHARMACOLOGICAL TEST 4

Anti-trichomonal test

Procedure of the test:

The compound under test was dissolved in aseptic water, and filtered aseptically to prepare a two fold dilution series. Each 2.6 ml ASAMI medium containing 20% of the horse serum were respectively taken into small test tubes. Onto the medium, there were incubated 0.3 ml of the two fold dilution solution of the compounds and 0.1 ml of the suspension of the ASAMI medium of Trichomonas vaginalis which was cultured at 37° C. for 3 days respectively. Incubation was carried out at 37° C. for 3 days to determine the minimal inhibitory concentration.

RESULT OF THE TEST

It was recognized that the compound A of this invention exhibits the minimal inhibitory concentration of 200 $\mu$g/ml and has anti-trichomonal activity.

In view point of the results of the pharmacological tests 1 – 4, it was found that the compound A of this invention has excellent antifungal, antibacterial and anti-trichomonal activities. It is seen that the antifungal activity of the compound A is not affected by the incubation temperature and addition of serum, and particularly, the compound (A) is effective against Candida albicans, Cryptococcus neoformans and the like. The compound according to this invention represented by the compound (A) of this invention has excellent antifungal, antibacterial and anti-trichomonal activities, hereinbefore mentioned. It is therefore concluded that the compound according to this invention is effective to treatment of candidiasis such as digestive tract-candidiasis, cutaneous candidiasis, vaginal candidiasis, cryptococcosis, trichomoniasis and mixed infection of those with various bacteria.

Following Examples will serve to illustrate the preparation of the compounds of the present invention.

EXAMPLE 1

Preparation of 1,4-bis-(m,m'-amidinophenoxymethyl)-cyclohexane dihydrochloride

5 Grams of 1,4-bis-(m,m'-cyanophenoxymethyl)-cyclohexane are thoroughly pulverized, which are then added to a mixed solvent consisting of 50 ml of dried chloroform and 5 ml of absolute ethanol. Dried gaseous hydrogen chloride is passed under the ice-cooling to the mixture, until the gas is saturated. The vessel for the mixture is sealed, followed by allowing to stand for a week at a room temperature. The reaction mixture is concentrated under a reduced pressure without heating, so that the hydrochloric acid is completely removed. Thereafter, the residue is dissolved in 80 ml of methanol. The solution is saturated with dried gaseous ammonia at a room temperature, is heated under reflux for one hour, and is concentrated to form a crystalline mass, which is then recrystallized from 90% ethanol-water to obtain the desired compound as white needles.

Yield: 4 g.
Melting Point: 290° – 292° C
Elementary analysis of the compound having a presumed formula $C_{22}H_{28}N_4O_2 \cdot 2HCl$ gave:

|  | C | H | N |
|---|---|---|---|
| Calculated (%) | 58.32 | 6.67 | 12.36 |
| Found (%) | 58.02 | 6.92 | 12.32 |

The starting material, 1,4-bis-(m,m'-cyanophenoxymethyl)-cyclohexane used with this example is produced by the following steps:

4.8 Grams of meta-cyanophenol and 6 g. of 1,4-bis-(methanesulfonyloxy methyl)-cyclohexane are added to 50 ml of methanol containing 2.65 g. of sodium ethylate. To the solution are further added 50 ml of dimethyl formamide, and the whole is heated under reflux for two hours. The reaction solution is poured into water, and the resulting crystalline substance is filtered and washed with water. After drying, the substance is recrystallized from chloroform-methanol, to obtain white granule.

Yield: 5 g.
Melting Point: 182° – 183° C.
Elementary analysis of the compound having a presumed formula: $C_{22}H_{22}N_2O_2$ gave:

|  | C | H | N |
|---|---|---|---|
| Calculated (%) | 76.27 | 6.40 | 8.09 |
| Found (%) | 75.91 | 6.41 | 8.10 |

EXAMPLE 2

Preparation of bis-(m,m'-amidinophenoxy)-para-xylene dihydrochloride

5 Grams of bis-(m,m'-cyanophenoxy)-para-xylene are pulverized, which are then added to a mixed solvent consisting of 50 ml of dried chloroform and 5 ml of absolute ethanol. Dried gaseous hydrogen chloride is passed under the ice-cooling to the mixture, until the gas is saturated. The vessel for the mixture is sealed, and allowed to stand for a week at a room temperature. The reaction mixture is concentrated under a reduced pressure without heating, so that the hydrochloric acid is thoroughly removed. The residue is then dissolved in 80 ml of methanol. The solution is saturated with dried gaseous ammonia at a room temperature, is heated under reflux for one hour, and is concentrated to form a crystalline mass, which is then recrystallized from ethanol-water to obtain the desired compound as white needles.

Yield: 2.5 g.
Melting Point: 298° – 300° C.
Elementary analysis of the compound having a presumed formula $C_{22}H_{22}N_4O_2 \cdot 2HCl$ gave:

|  | C | H | N |
|---|---|---|---|
| Calculated (%) | 59.06 | 5.41 | 12.52 |
| Found (%) | 58.99 | 5.43 | 12.29 |

The starting material, bis-(m,m'-cyanophenoxy)-para-xylene used with this example is produced by the following steps:

13.2 Grams of meta-cyanophenol are dissolved in 200 ml of ethanol containing 7.5 g. of sodium ethylate. To the solution are added 8.7 g. of α,α'-dichloro-para-xylene, and the whole is heated under reflux with stirring for two hours. After cooling, the reaction solution is poured into water, the resulting crystalline substance is filtered and washed with water. After drying, the substance is recrystallized from chloroform-methanol, to obtain white powder.

Yield: 14.5 g.
Melting Point: 174° – 175° C.
Elementary analysis of the compound having a presumed formula $C_{22}H_{16}N_2O_2$ gave:

|  | C | H | N |
|---|---|---|---|
| Calculated (%) | 77.63 | 4.74 | 8.23 |
| Found (%) | 77.85 | 4.81 | 8.15 |

EXAMPLE 3

Preparation of bis-(m,m'-amidinophenoxy)-2,3,4,6-tetrachloro-meta-xylene-dihydrochloride-monohydrate The procedure in Example 1 is repeated, except for the use of 5 g. of bis-(m,m'-cyanophenoxy)-2,3,4,6-tetrachloro-meta-xylene having the melting point of 229° C. The resulting crystalline mass is recrystallized from ethanol-water, to obtain the desired compound as white powdery substance.

Yield: 2.2 g.
Melting Point: 289° – 291° C.
Elementary analysis of the compound having a presumed formula $C_{22}H_{18}N_4O_2 \cdot 2HCl \cdot H_2O$ gave:

|  | C | H | N |
|---|---|---|---|
| Calculated (%) | 43.81 | 3.68 | 9.29 |
| Found (%) | 44.01 | 3.81 | 9.23 |

EXAMPLE 4

Preparation of 1,4-bis-(m,m'-amidinophenoxy)-2-butene.dimethane sulfonate

The procedure in Example 1 is repeated, except for the use of 5 g. of bis-(m,m'-cyanophenoxy)-2-butene having the melting point of 156° – 157° C., to obtain bis-(m,m'-amidinophenoxy)-2-butene.hydrochloride.

The resulting compound is dissolved in water. To the solution is added sodium carbonate to adjust its alkalinity to pH 9. The resulting crystalline mass is filtered, and is suspended in ethanol. To the suspension is added ethanol containing methane sulfonic acid, so as to dissolve all the crystalline mass. After concentration, the mass is recrystallized from ethanol-water, to obtain the desired compound as white granule.

Yield: 2.2 g.
Melting Point: 204° – 205° C.
Elementary analysis of the compound having a presumed formula $C_{18}H_{20}N_4O_2 \cdot 2CH_3SO_3H$ gave:

|  | C | H | N |
| --- | --- | --- | --- |
| Calculated (%) | 46.50 | 5.46 | 10.84 |
| Found (%) | 46.16 | 5.39 | 10.70 |

EXAMPLE 5

Preparation of bis-(m,m'-amidinophenoxy)-1,4-butane.dimethane sulfonate

The procedure in Example 1 is repeated, except for the use of 4 g. of bis-(m,m'-cyanophenoxy)-1,4-butane, to obtain bis-(m,m'-amidinophenoxy)-1,4-butane-dihydrochloride.

The resulting compound is dissolved in water. To the solution is added 10% solution of sodium carbonate, so that its alkalinity may amount to pH 9. The resulting crystalline mass is filtered, and suspended in 30 ml of ethanol. To the suspension is added ethanol containing methane sulfonic acid, until the solution shows slight acidity. The resulting crystalline substance is filtered, and is recrystallized from ethanol, to obtain the desired compound as colourless granules.

Yield: 1.5 g.
Melting Point: 217.5° – 218° C.
Elementary analysis of the compound having a presumed formula $C_{18}H_{22}N_4O_2 \cdot 2CH_3SO_3H$ gave:

|  | C | H | N |
| --- | --- | --- | --- |
| Calculated (%) | 46.32 | 5.83 | 10.80 |
| Found (%) | 46.58 | 5.88 | 10.77 |

The following Table 6 illustrates Examples 6 - 10 wherein data are given in the compound of this invention.

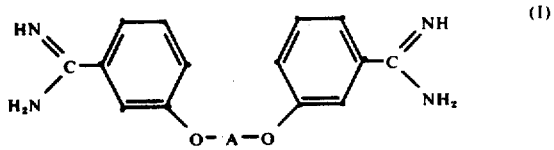
(I)

Table 6

| Ex. No. | A | Molecular Formula Melting Point (°C) | Elementary Analysis Calculated (%) Found (%) | | |
| --- | --- | --- | --- | --- | --- |
| | | | C | H | N |
| 6 | –CH₂–(phenyl 1,3)–CH₂– | $C_{22}H_{22}N_4O_2 \cdot 2HCl \cdot 2H_2O$ 149 – 150°C. | 54.66 55.01 | 5.84 5.84 | 11.59 11.73 |
| 7 | –CH₂–(tetrachlorophenyl)–CH₂– | $C_{22}H_{18}N_4O_2Cl_4 \cdot 2HCl \cdot H_2O$ >300°C. | 43.81 44.20 | 6.68 6.63 | 9.29 9.11 |
| 8 | –(CH₂)₂S(CH₂)₂– | $C_{18}H_{18}N_4S \cdot 2HCl \cdot 2H_2O$ 90°C. | 46.25 46.34 | 6.39 6.03 | 11.99 12.04 |
| 9 | –(CH₂)₃– | $C_{18}H_{14}N_4O_2 \cdot 2HCl \cdot H_2O$ 122 – 123°C. | 52.91 53.36 | 6.54 6.47 | 12.98 13.22 |
| 10 | –(CH₂)₄– | $C_{20}H_{26}N_4O_2 \cdot 2HCl$ 250 – 251°C. | 56.21 56.44 | 6.60 6.58 | 13.11 13.30 |

What is claimed is:

1. Bis-(meta-amidinophenoxy)-compound having the general formula:

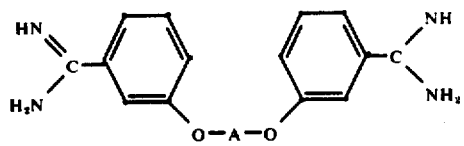

wherein A represents the chain residue

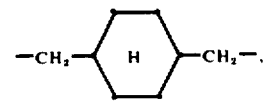

and its pharmacologically acceptable acid addition salts.
2. Bis-(meta-amidinophenoxy)-compound as claimed in claim 1, wherein the compound is represented by the following chemical formula:
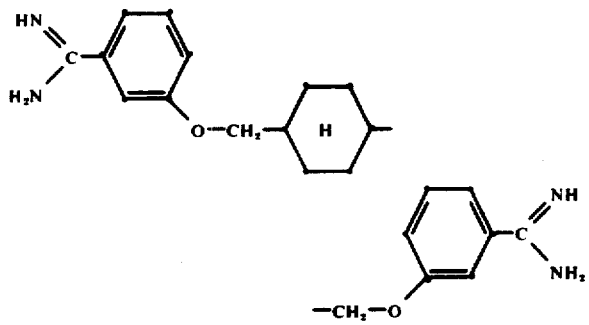
* * * * *